US008425400B2

(12) United States Patent
Goria et al.

(10) Patent No.: US 8,425,400 B2
(45) Date of Patent: Apr. 23, 2013

(54) IMPLANT FOR SUPPORTING THE URETHRA OF A MAN AND A SURGICAL KIT FOR TREATING INCONTINENCE IN A MAN AND INCLUDING SUCH AN IMPLANT

(75) Inventors: Vincent Jean-Claude Goria, Lyons (FR); Philippe Grise, Rouen (FR)

(73) Assignee: CL Medical, Sainte Foy les Lyon (FR)

( * ) Notice: Subject to any disclaimer, the term of this patent is extended or adjusted under 35 U.S.C. 154(b) by 1021 days.

(21) Appl. No.: 12/222,793

(22) Filed: Aug. 15, 2008

(65) Prior Publication Data

US 2009/0048479 A1    Feb. 19, 2009

Related U.S. Application Data

(60) Provisional application No. 60/935,551, filed on Aug. 17, 2007.

(30) Foreign Application Priority Data

Aug. 17, 2007   (FR) .................................. 07 05884

(51) Int. Cl.
*A61F 2/00*     (2006.01)
(52) U.S. Cl.
USPC ............................. 600/37; 600/30; 606/151
(58) Field of Classification Search .............. 600/29–32, 600/37; 128/897–899; 606/151
See application file for complete search history.

(56) References Cited

U.S. PATENT DOCUMENTS

| | | | |
|---|---|---|---|
| 6,039,686 A | 3/2000 | Kovac | |
| 6,042,534 A * | 3/2000 | Gellman et al. | ................ 600/30 |
| 6,042,536 A | 3/2000 | Tihon et al. | |
| 6,382,214 B1 | 5/2002 | Raz et al. | |
| 6,383,201 B1 * | 5/2002 | Dong | ............................ 606/151 |
| 6,408,656 B1 | 6/2002 | Ory et al. | |
| 6,599,318 B1 | 7/2003 | Gabbay | |
| 6,612,977 B2 * | 9/2003 | Staskin et al. | .................. 600/30 |
| 6,652,450 B2 | 11/2003 | Neisz et al. | |
| 6,695,855 B1 | 2/2004 | Gaston | |
| 7,175,591 B2 | 2/2007 | Kaladelfos | |
| 7,407,480 B2 | 8/2008 | Staskin et al. | |
| 2002/0138025 A1 | 9/2002 | Gellman et al. | |
| 2003/0045774 A1 | 3/2003 | Staskin et al. | |
| 2004/0039246 A1 * | 2/2004 | Gellman et al. | ................. 600/30 |

(Continued)

FOREIGN PATENT DOCUMENTS

| | | |
|---|---|---|
| EP | 1342450 | 1/2007 |
| EP | 1797842 | 6/2007 |

(Continued)

*Primary Examiner* — Charles A Marmor, II
*Assistant Examiner* — Carrie R Dorna
(74) *Attorney, Agent, or Firm* — Dowell & Dowell, PC

(57) ABSTRACT

An implant for supporting a urethra of a man which includes two elongate flexible strips that are substantially inextensible in length between opposite ends thereof and that include middle portions that are disposed adjacent to one another in side by side relationship such that a side edge of each strip faces towards the other strip, and wherein the strips are connected to each other at the middle portions, and wherein the strips have intermediate portions that extend between the middle portion and each opposite end of each strip along which the strips are separate from each other. The implant supports the urethra in such a manner that the two strips may be placed under tension independently of each other with the middle portions thereof supporting the urethra over a total width of the strips.

16 Claims, 5 Drawing Sheets

U.S. PATENT DOCUMENTS

| | | | |
|---|---|---|---|
| 2004/0144394 A1* | 7/2004 | Dauner et al. | 128/885 |
| 2004/0215219 A1* | 10/2004 | Eldridge et al. | 606/151 |
| 2005/0070829 A1 | 3/2005 | Therin et al. | |
| 2005/0222591 A1 | 10/2005 | Gingras et al. | |
| 2005/0250977 A1* | 11/2005 | Montpetit et al. | 600/29 |
| 2006/0195010 A1 | 8/2006 | Arnal et al. | |
| 2006/0252980 A1 | 11/2006 | Arnal et al. | |
| 2006/0287571 A1* | 12/2006 | Gozzi et al. | 600/30 |
| 2008/0210247 A1 | 9/2008 | De Leval | |

FOREIGN PATENT DOCUMENTS

| | | |
|---|---|---|
| FR | 2792824 | 11/2000 |
| WO | 2007/016698 | 2/2007 |
| WO | WO2007149593 A2 * | 12/2007 |

* cited by examiner

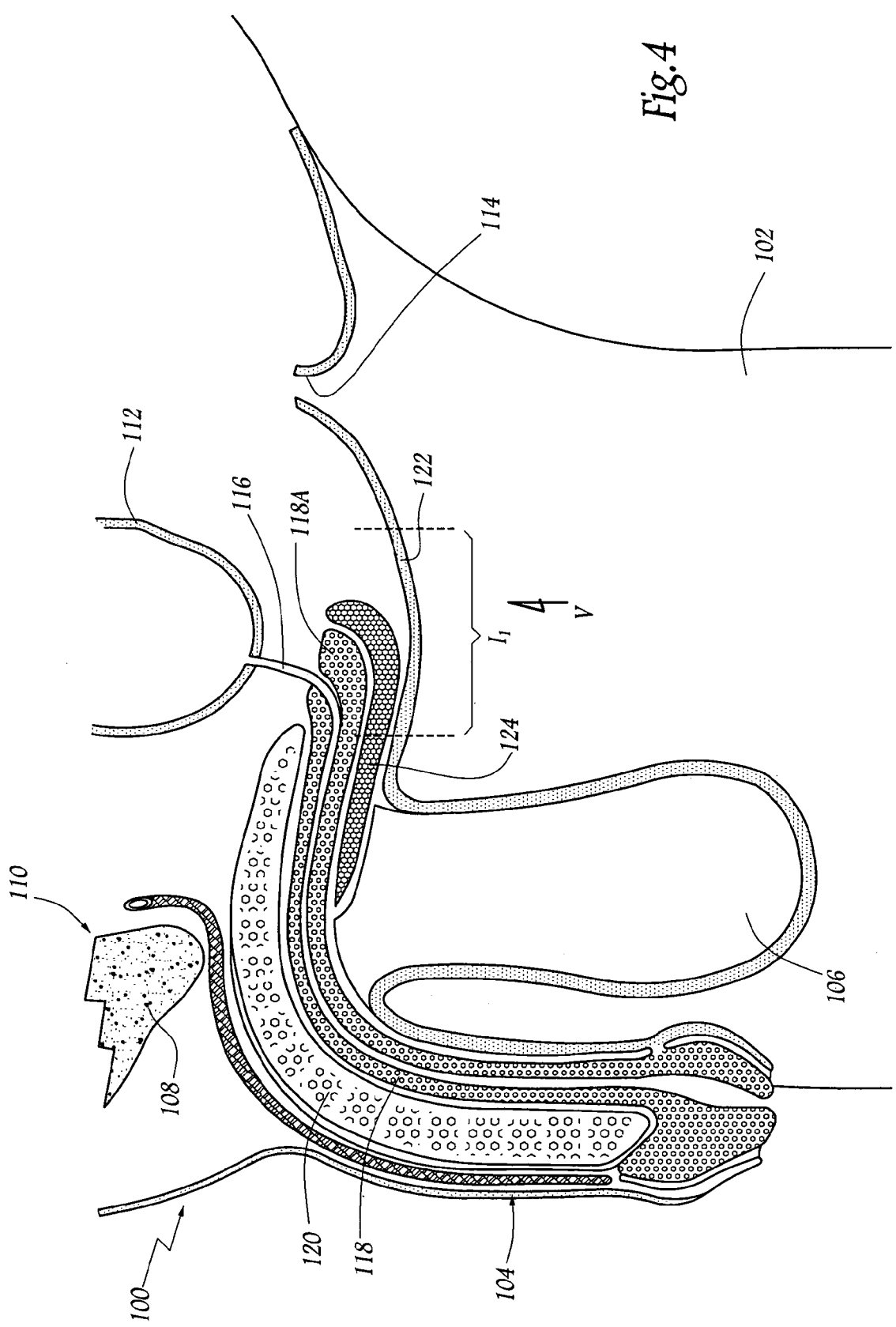

IMPLANT FOR SUPPORTING THE URETHRA OF A MAN AND A SURGICAL KIT FOR TREATING INCONTINENCE IN A MAN AND INCLUDING SUCH AN IMPLANT

BACKGROUND OF THE INVENTION

1. Field of the Invention

The present invention relates to an implant for supporting the urethra of a man in order to treat urinary incontinence. The invention also relates to a surgical kit and to a method of treating urinary incontinence in a man, using such an implant.

2. Description of the Related Art

Urinary incontinence in men after prostatectomy constitutes an invalidating disorder that spoils quality of life even if the incontinence is moderate. The number of incontinent patients has increased over the last few years with the arrival of techniques for early detection of cancer of the prostate and with larger numbers of total prostatectomies being performed. Even though recent surgical techniques enable the sphincter to be preserved better, leaks of urine can occur in a non-negligible percentage of cases: these leaks of urine are associated with the surgical technique that causes the bottom portion of the prostate to be sectioned in the immediate vicinity of the sphincter, and they can also be made worse by specific elements associated with the patient, such as a short urethra, a sphincter that is weak or easily tired, etc.

For patients suffering from urinary incontinence in spite of sphincter re-education, the surgical treatment that has been commonly been used over the last few years consists in implanting an artificial sphincter. That operation limits incontinence very significantly, but suffers from major drawbacks: the patient needs to manipulate a pump on each urination, the implanted equipment is burdensome, and the repeat surgery rate is high.

A new surgical treatment technique has thus appeared recently, namely placing an implant that provides support under the urethra, which implant is generally in the form of a net or in a form of a plate. That kind of net needs to be firmly secured to anatomical structures of the patient in order to guarantee effective support of the urethra and thus correct incontinence. The plate is thus either suspended by threads rising up either side of the bladder, under or behind the pubis, and with terminal fastenings in the patient's abdominal wall, or else they are directly secured to screws in the patient's ischio-pubic bony branches. In the first configuration, the risk of perforating the bladder is real, and in the second the surgery is more complex and exposes the patient to a risk of ostitis. Either way, the presence of the implanted plate can lead to transient postoperative perineal discomfort, or indeed to permanent perineal pain. Furthermore, even if the success rate of the treatment is high in the short term, it tends to fall off significantly over time.

Simultaneously, equipment and methods for treating incontinence in women have recently been developed with success. In particular, EP-A-1 342 450 in the name of the present Applicant discloses a sub-urethral support strip that can be implanted in various ways including via a so-called "trans-obturator" approach, i.e. by passing the free end portions of the strip through the respective obturator foramens in a patient's ilium, thereby causing the urethra to be suspended on the longitudinally middle portion of the strip. The advantages of this trans-obturator implantation approach are real, since they run no risk of perforating the bladder and they do not require any fastening to bone, with only the free ends of the strip being secured in the patient's abdomen.

SUMMARY OF THE INVENTION

The object of the present invention is to provide an implant for supporting the urethra of a man, that is effective in treating urinary incontinence, that is easy to manipulate while it is being implanted, and that can be put into place via a trans-obturator approach.

To this end, the invention provides an implant for supporting the urethra of a man for treating urinary incontinence, the implant being characterized in that it comprises two elongate flexible strips that are substantially inextensible in their long direction and that comprise firstly respective middle portions, that are disposed side by side in adjacent manner along the side edge of each strip that faces towards the other strip, and where said strips are mechanically connected to each other, and secondly respective intermediate portions, that extend between the middle portion and each longitudinal end of each strip, and where the strips are separate from each other.

The implant of the invention, which corresponds to a kind of double strip, can be implanted in the proximity of sub-urethral tissue, in particular in the proximity of the spongy body surrounding the urethra and the cavernous bodies disposed on either side of the spongy body. Its specific form as a double strip makes it possible simultaneously to support the urethra firmly and effectively and to implant the implant by the trans-obturator approach. Although, at first sight, the trans-obturator implantation approach used with the implant of the invention can be thought of as much the same as the trans-obturator approach implemented when treating urinary incontinence in woman, it should not be forgotten that the constraints on putting an implant into place in a man are quite different from those on putting one into place in a woman: in a woman, the sub-urethral support strips are implanted while remaining flexible in the vicinity of the pelvic floor, since the lower abdominal anatomy of a woman does not require and cannot accommodate any stress that is too firm. In contrast, in a man, the spongy body surrounding the urethra presents a degree of firmness, such that effective support of the urethra for treating incontinence requires clear thrust to be applied, with the implant being under tension against the spongy body, or more generally the tissue under the urethra, which would, a priori, dissuade the person skilled in the art from transposing to man the trans-obturator technique that has been developed for woman. Under such conditions, one of the ideas on which the invention is based consists in making provision such that the width of the middle zone of the implant, i.e. its dimension measured in a direction substantially perpendicular to the longitudinal direction of the two strips forming the implant, corresponds to the sum of the individual widths of the strips, because the middle portions of the strips are juxtaposed edge to edge. This double width of the middle zone of the implant, compared with the remainder of the implant, makes it possible to achieve urethral support over twice the extent that can be obtained using only one of the two strips individually. As a result, when the implant is implanted, the middle portions of the two strips support the spongy body of the patient over a considerable extent, and consequently do so firmly, including supporting the end bulb of the spongy body. Simultaneously, each of the intermediate portions of each of the two strips can easily be passed through one of the obturator foramens of the patient's ilium because of the elongate shape and narrow width of the strip.

In addition, the specific structure of the implant in accordance with the invention makes it possible to apply tension to each of the two strips differently. On implanting the implant, traction on the two intermediate portions of each strip gives rise to a transverse support effect for the urethra in the bottom of the U-shape formed by the middle portion of the corresponding strip around the tissue beneath the urethra, thereby compressing the urethra so as to obstruct it in part and thus treat incontinence. This tensioning of each strip is associated with the property of the strip being inextensible in its long direction. It will be understood that on implantation, the surgeon can apply differing intensities of traction to each of the strips so as to generate a support effect that is stronger in the middle portion of one of the strips compared with the middle portion of the other strip. This disposition can be of advantage, for example, particularly with a patient who has been subjected to a prostatectomy: under such circumstances, the surgeon can apply stronger tension to the posterior strip than to the anterior strip, i.e. stronger tension to the strip that is closer to the patient's bladder. In general, the implant of the invention enables the surgeon to adjust the tensioning of the implant in differing and independent manner for each of the two strips of the implant, thereby obtaining fine control over the urethral support effect.

In an advantageous dimensional configuration, the middle portions of the strips present a longitudinal size that is less than 8 centimeters (cm), preferably that lies in the range 2 cm to 4 cm.

As a result, the middle zone of the implant presents a length that is sufficient to obtain the desired urethral support effect, while being easy to put into place when implanting the implant. The anatomical structures of the patient can then be cleared in depth without complicating the acts performed by the surgeon, since on either side of the middle zone of the implant, the intermediate portions of the two strips are narrow in width, in particular compared with implants of the plate type.

In a practical embodiment, that is both easy to make and to implant, the middle portion and the intermediate portions of each strip present a substantially constant width that does not vary along the length of the strip.

Advantageously, the two strips are also mechanically connected to each other at their two longitudinal ends, each of which is provided with a joint fastener element for connecting both strips together to an instrument for implanting the implant, in particular an implantation needle.

By means of this arrangement, the two intermediate portions of the strips situated on the same side of the middle portions are handled together while the implant is being implanted, in particular for the purpose of putting these two intermediate portions into place through one of the obturator foramens of the patient's ilium in a single pass.

According to other characteristics of the implant in accordance with the invention that are advantageous and that may be taken in isolation or in any technically feasible combination:

- each strip is essentially constituted by a yarn knit comprising longitudinal reinforcing chains and an intermediate trellis connecting the chains together transversely;
- at each longitudinal end of the strips the knits of the two strips are sewn to the joint fastener element;
- at least one of the chains belonging to the middle portion of one of the strips is connected by stitching to at least one of the chains belonging to the middle portion of the other strip;
- the chains of the middle portions of the two strips are connected together by two lines of stitches that extend transversely relative to the chains and that define respective longitudinal ends of the middle portions; and
- each strip is bordered by two lateral fringes for clinging to tissues in which the implant is implanted, and the two fringes that face each other in the middle portions of the two strips are intermingled.

The invention also provides a surgical kit for treating urinary incontinence in a man, the kit being characterized in that it comprises:

- an implant for supporting the urethra of a patient, as defined above; and
- at least one instrument for implanting the implant, in particular an implantation needle adapted to co-operate with one and/or the other of the two joint fastener elements.

The invention also provides a surgical method for treating urinary incontinence in a man, by means of an implant for supporting the urethra of a patient, the implant comprising two elongate flexible strips that are substantially inextensible in their long direction and that comprise firstly respective middle portions that are disposed side by side in adjacent manner along the side edge of each strip that faces towards the other strip, and where said strips are mechanically connected to each other, and secondly respective intermediate portions that extend between the middle portion and each longitudinal end of each strip, and where the strips are separate from each other;

said method comprising peroperative steps consisting in:

i) vertically incising the skin and the subcutaneous fat in the perineal region of the patient between his scrotum and his anus, as far as the bulb of his urethral spongy body, while preserving said spongy body;

ii) in the perineal incision made during step i), separating on either lateral side of the urethral spongy body, the two cavernous bodies of the patient;

iii) sagittally incising the perineal membrane between each of the two cavernous bodies and the urethral spongy body;

iv) putting the implant into place in the patient's body in such a manner that the middle portions of the strip extend under and across the urethral spongy body, while on either side of these middle portions, the corresponding intermediate portions of the two strips extend from the corresponding incision in the perineal membrane made during step iii) to the root of the corresponding thigh of the patient, passing via the corresponding obturator foramen of the patient's ilium, the longitudinal ends of the strip extending outside the patient from the roots of the thighs;

v) pulling on the intermediate portions of the strips in such a manner as to cause the middle portions to bear under tension against the urethral spongy body, the intensities of the traction applied respectively to the two strips being adjustable independently of each other; and vi) cutting off the portions of the strip that extend out from the roots of the thighs and closing the perineal incision made in step i).

BRIEF DESCRIPTION OF THE OF THE DRAWINGS

The invention can be better understood on reading the following description given purely by way of example and made with reference to the drawings, in which:

FIG. 4 is a diagrammatic sagittal section of the lower abdomen of a man;

DETAILED DESCRIPTION OF THE PREFERRED EMBODIMENTS OF THE INVENTION

Figure 1:
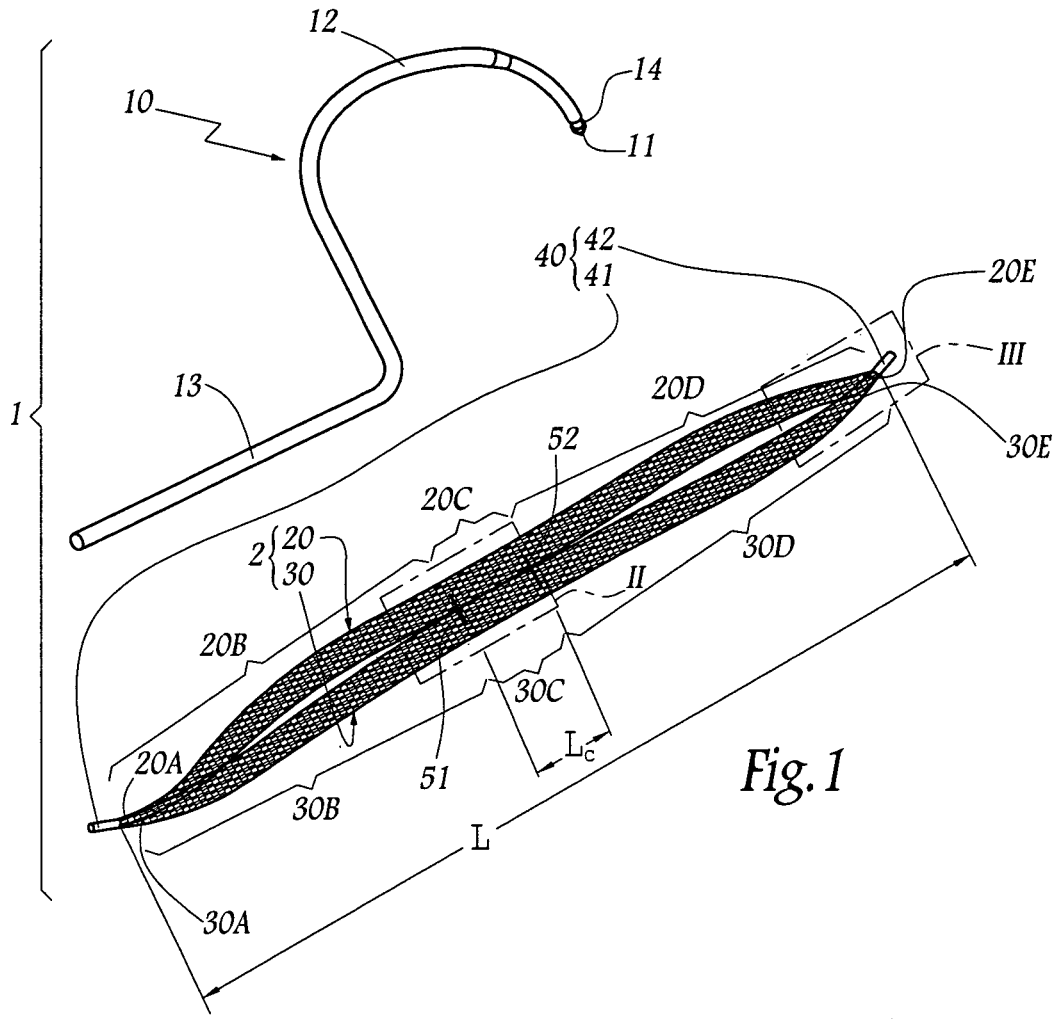
FIG. 1 is a diagrammatic perspective view of a surgical kit of the invention.

FIG. 1 shows a kit 1 for treatment of urinary incontinence in a man. The kit 1 comprises an implant 2 for supporting the urethra of a patient, together with a curved needle 10.

The needle 10 is made of surgical steel and comprises, in succession lengthwise: a pointed end 11; a curved main portion 12; and a base portion 13 serving more particularly for grasping the needle. An optional handle (not shown) can thus be removably fitted to the base portion 13. The needle used may present a variety of embodiments, in particular concerning its curved portion 12: in the example shown in FIG. 1, this portion 12 lies generally in a plane, with a profile in said plane constituting a portion of a circle, however other shapes could also be envisaged, such as a shape forming a portion of a helix.

The implant 2 essentially comprises two distinct strips 20 and 30 and means 40 for securing the implant to the needle 10, as described in greater detail. In the example under consideration, the strips 20 and 30 are identical to each other.

Figure 3:
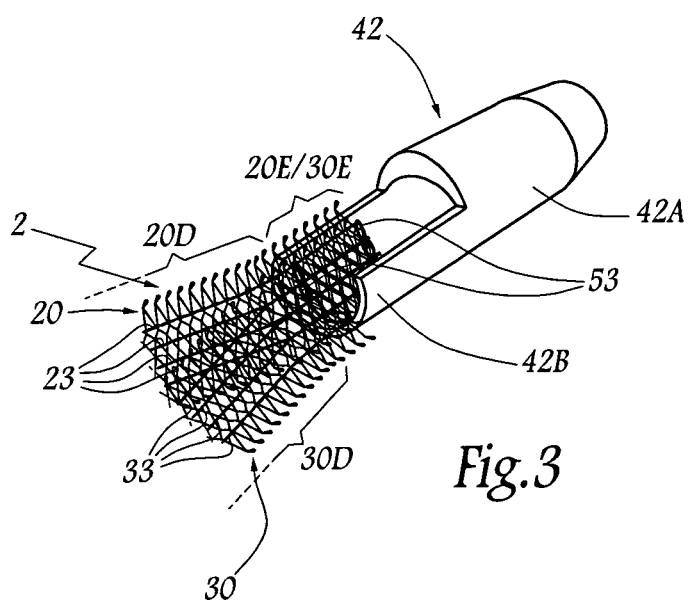
FIG. 3 is a diagrammatic perspective view showing a detail of box III of FIG. 1.
Figure 2:
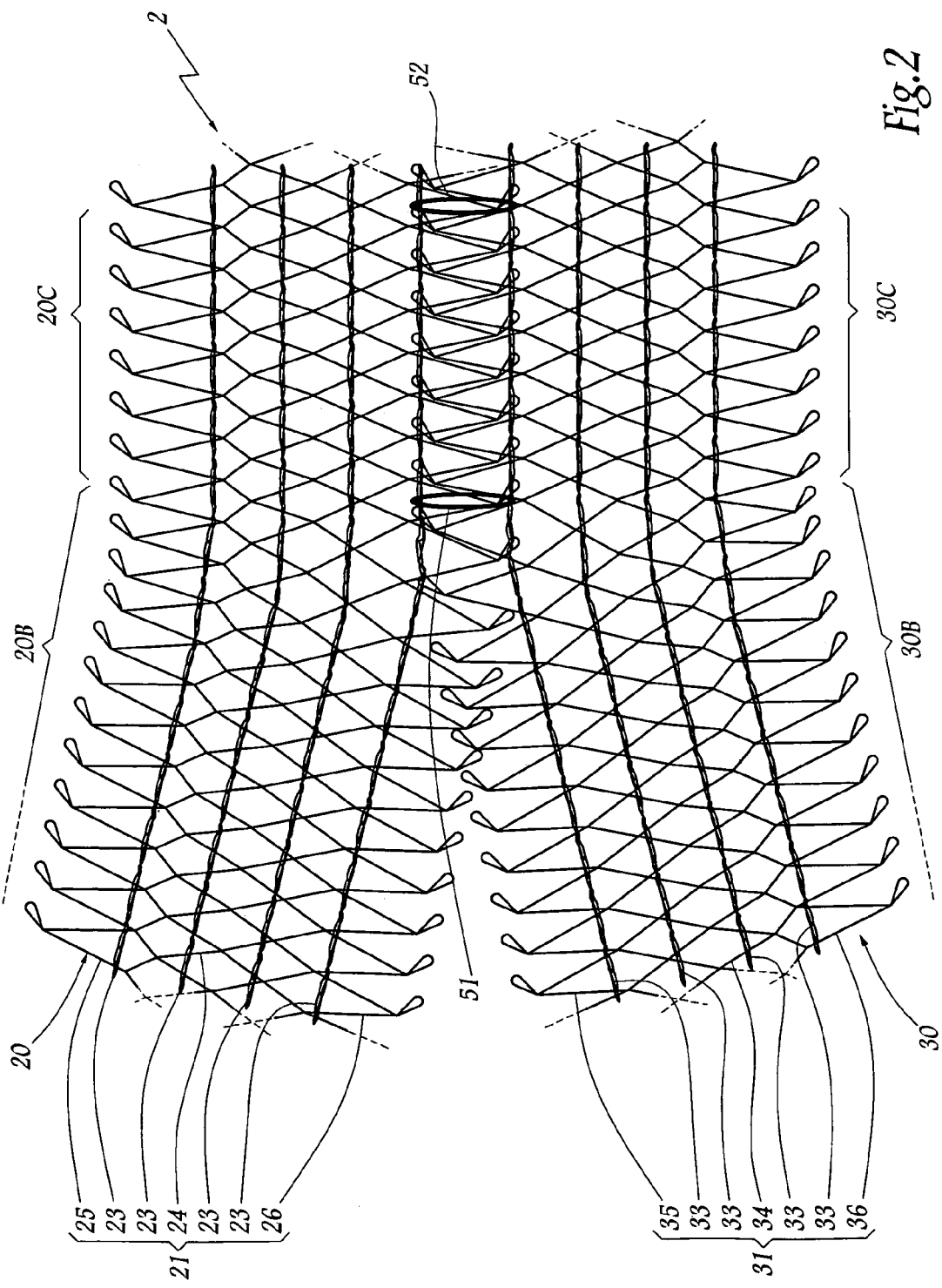
FIG. 2 is a diagrammatic elevation view showing a detail in box II of FIG. 1.
Figure 5:
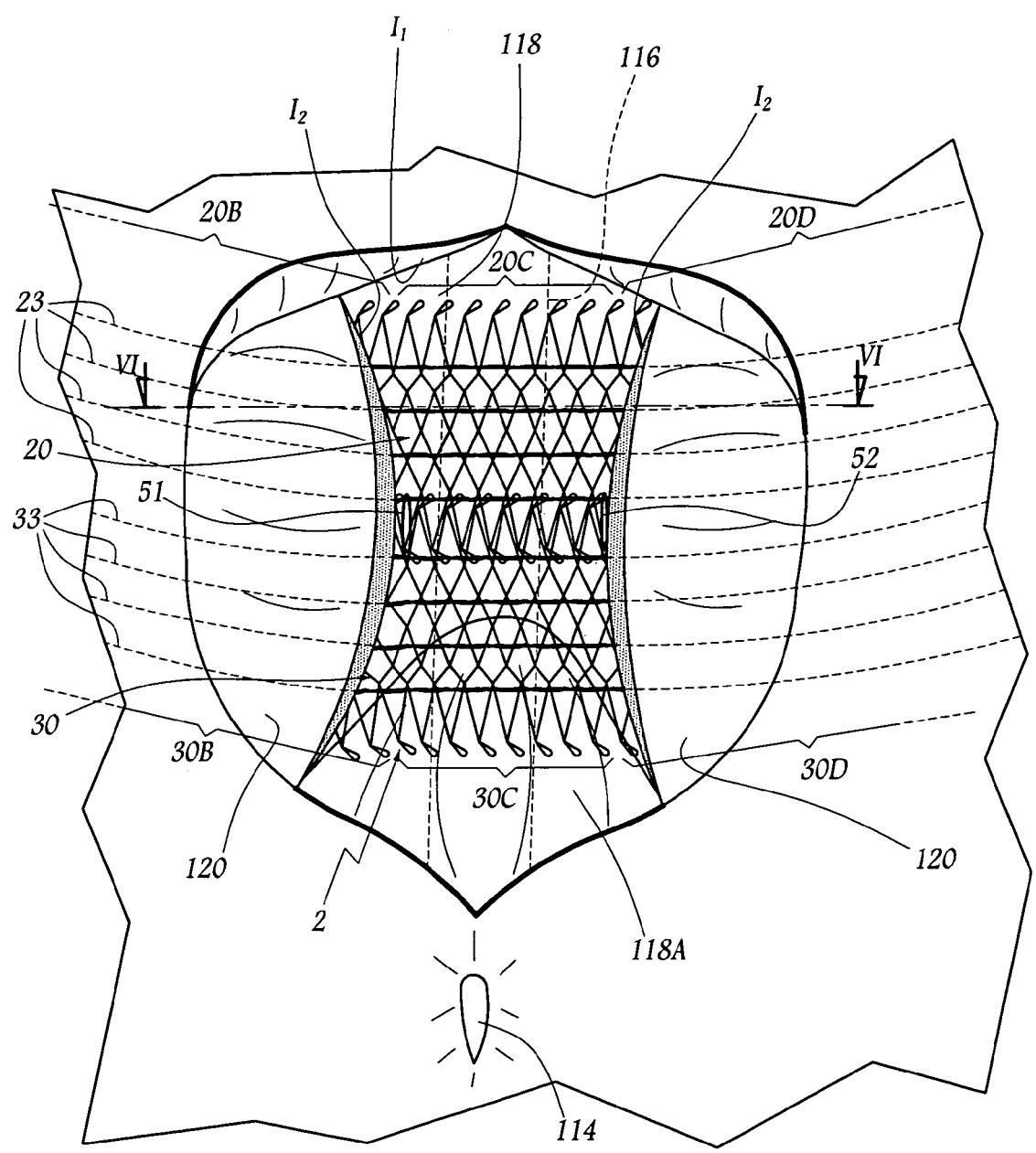
FIG. 5 is an elevation view looking along arrow V in FIG. 4 showing the implementation of the treatment kit of FIG. 1.
Figure 6:
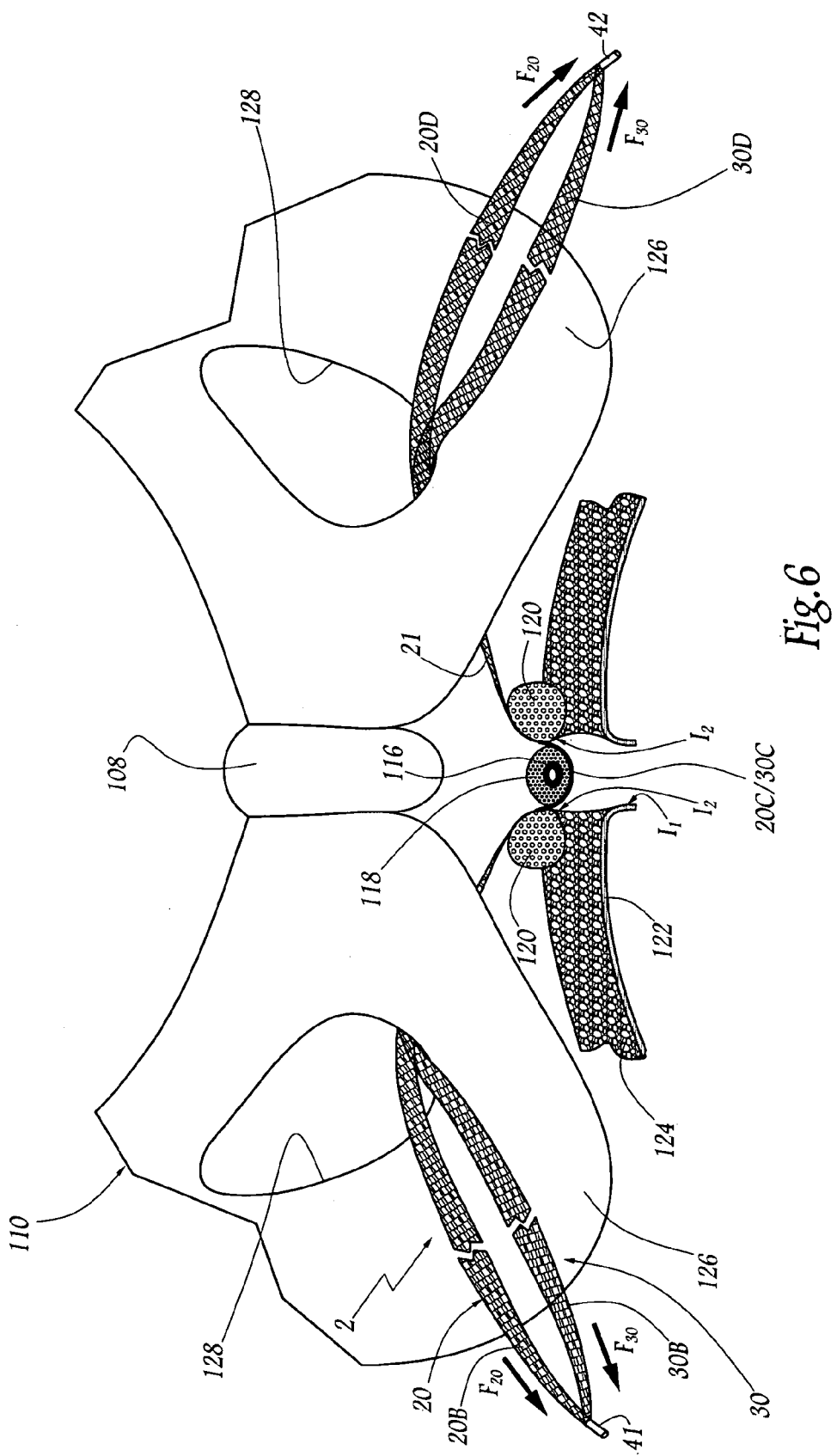
FIG. 6 is a diagrammatic section on line VI-VI of FIG. 5.

Each strip 20, 30 is constituted, along its entire length, by a knit 21, 31 of biocompatible yarn, preferably constituted by monofilaments of polypropylene. In FIGS. 1 and 6, the structure of the knit is not visible, with the strips being represented in highly diagrammatic manner for the purposes of illustration, whereas the knits are shown in FIGS. 2, 3, and 5 in a way that enables details of their structure to be seen. Each knit 21, 31 comprises firstly four knitted longitudinal chains 23, 33 that are parallel to one another and that form the reinforcement of the knit, and secondly an intermediate meshed trellis 24, 34 interconnecting the chains transversely. This structure for the knit enables it to be both flexible and non-extensible, so that it can be put into place in soft tissues of the patient, adapting to the shape of those tissues, while ensuring that the knit presents substantially no elasticity in the longitudinal direction of the strip, so as to enable it to be implanted under a high level of longitudinal tension.

Each knit 21, 31 also includes two opposite side fringes 25 and 26, 35 and 36 running all along the two sides of each of the strips 20 and 30 like selvages. Each fringe 25, 26, 35, 36 is constituted by yarns of the knit 21, 31 extending outwards from the strip transversely relative to the corresponding edge chain 23, 33. These fringes are thus suitable for clinging to tissue when the implant 2 is implanted in the body of the patient. Each yarn making up these fringes advantageously presents the shape of a closed loop in order to limit irritating the tissue when the implant is put into place.

Concerning the connection between the two strips 20 and 30 when the implant 2 is ready for handling by a surgeon in order to be implanted, each strip comprises five successive portions 20A to 20E and 30A to 30E along its length, as specified below.

The strips 20 and 30 are connected mechanically to each other simultaneously in their middle portions 20C and 30C, at one of their longitudinal ends referenced 20A, 30A, and at their opposite longitudinal ends 20E, 30E.

More precisely, in each of the middle portions 20C and 30C of the strips 20 and 30, two of the edge chains 23 and 33 belonging respectively to the strips 20 and 30 and extending beside each other are interconnected by stitching via two lines of stitches 51 and 52 that are spaced apart from each other in the longitudinal direction of the strips, as can be seen in FIG. 1 and as shown in more detail in FIG. 2. Each line 51, 52 extends lengthwise in a direction that is substantially perpendicular to the two above-mentioned chains, such that the middle portions 20C and 30C of the strips extend lengthwise adjacent to each other with their respective edge chains 23 and 33 facing each other in parallel. Between these two edge chains that are facing each other, the corresponding portions of the fringes 26 and 35 are intermingled, with the yarns constituting these fringes being tangled together, but nevertheless without the yarns becoming knotted to one another.

The ends 20A and 30A of the strips 20 and 30 are connected together by an element 41, while the ends 20E and 30E are connected together by another element 42, as can be seen in FIG. 1, and as shown in greater detail for the element 42 in FIG. 3. In the embodiment under consideration, the elements 41 and 42 are identical: each of these elements is in the form of a rigid hollow sleeve having an end portion pointing away from the strips 20 and 30 (referenced 42A for the element 42 in FIG. 3) that is adapted to snap around the pointed end 11 of the needle 10, in particular into a circumferential groove 14 formed in the body of the needle in the vicinity of said end. The other end portion of each element 41, 42, opposite from the above-mentioned end portion and referenced 42B for the element 42 in FIG. 3, is in the form of a length of tube with the ends of the strips 20A and 30A or 20E and 30E being sewn to the inside thereof, in particular via at least one line 53 of stitches that serves to assemble the chains 23 and 33 to the wall of the element 41, 42.

Thus, each element 41, 42 serves to connect both of the strips 20 and 30 to the needle 10, these two-elements thus forming part of the above-mentioned means 40. In order to ensure a compact configuration, the strip ends 20A and 30A, and 20E and 30E, are generally superposed one on the other inside the end portions 41B, 42B of their corresponding elements 41, 42, thereby also limiting the number of stitches in the line(s) 53 needed for mechanically securing the knits 21 and 31 to said elements.

Between its end 20A, 30A and its middle portion 20C, 30C, each strip 20, 30 defines an elongate intermediate portion 20B, 30B. Since the strips 20 and 30 are mechanically connected to each other, both in their middle portions 20C, 30C and in their end portions 20A, 30A, the intermediate strip portions 20B and 30B extend generally facing each other, while being separate from each other in the sense that they are not directly connected together, and are free to be moved apart from each other, as shown in FIGS. 1 and 2.

Between its end 20E, 30E and its middle portion 20C, 30C, each strip 20, 30 defines an elongate intermediate portion 20D, 30D. These intermediate portions 20D and 30D are functionally analogous to the intermediate portions 20B and 30B, such that in these portions 20D and 30D, the strips are separate.

To obtain the implant 2, a particularly advantageous method of fabrication consists in knitting the strips 20 and 30 simultaneously adjacent to each other lengthwise, with the fringe 26 intermingling with the fringe 35 over the full length of the strips. Thereafter, the strips are stitched to each other via the lines of stitches 51 and 52. The two strips are then separated from each other between their ends 20A, 30A and the line of stitches 51, and between their ends 20E, 30E and the line of stitches 52. To do this, the yarns constituting the selvages 26 and 35 are untangled by moving the strips transversely apart, beginning at the ends 20A and 30A, 20E and 30E and progressing towards the corresponding line of stitches 51 or 52. It can be understood that the lines of stitches 51 and 52 form stop zones when separating the two strips, such that the middle strip portions 20C and 30C remain parallel and adjacent, one alongside the other, and the fringe portions 36 and 25 extending along these middle portions remain intermingled with each other. The strip ends 20A and 30A are then stitched to the element 41, and the strip ends 20E and 30E are stitched to the element 42.

It can be understood from this example method of fabricating the implant 2, that the lines of stitched 51 and 52 define respectively, along the strips 20 and 30, the longitudinal ends of the middle portions 20C and 30C in the sense that between these two lines, the chains 23 and 33 of the knits 21 and 31 are held substantially parallel to each other and the fringes 36 and 25 continue to be intermingled, whereas on the side of the line of stitches 51 remote from the line 52, and on the side of the line of stitches 52 remote from the line 51, the knits 21 and 31 are separate, and in particular the fringes 36 and 25 are disengaged from each other, so as to form the intermediate strip portions 20B, 30B, 20D, and 30D. The effect of the middle strip portions 20C and 30C being held together by the lines of stitches 51 and 52 is associated in practice with the fact that the distance between two lines of stitches, i.e. the length $L_C$ of the middle portions 20C and 30C, is shorter than the length of either of the intermediate portions 20B, 30B, 20D, 30D, and in particular constitutes less than 20% of the total length L of the strips 20 and 30. In an advantageous embodiment, the length $L_C$ is less than 8 cm and is preferably equal to 3 cm±1 cm for anatomical reasons that are explained below.

In FIG. 4, there can be seen diagrammatically the lower abdomen 100 of a man, and in the background the outline of the upper portion of one of his thighs 102. In the sagittal plane corresponding to this figure, there can be seen in succession, going from the front towards the back of the patient, his penis 104, the outline of his scrotum 106, the pubis 108 of his ilium 110, his bladder 112, and his anus 114. The flow of urine from the bladder 112 out from the penis 104 takes place via the patient's urethra 116. The major longitudinal portion of the urethra is surrounded by the spongy body 118 of the penis 104, on either side of which there extend lengthwise the two cavernous bodies 120 of the penis. In FIG. 4, only one cavernous body is shown, it being understood that the two cavernous bodies are situated on either side in substantially symmetrical manner about the sagittal plane of the patient, while the urethra 116 and the spongy body 118 are generally centered on said plane.

There follows a description of a surgical method for treating urinary incontinence in the patient whose lower abdomen 100 is shown in FIG. 4, by means of the kit 1 that is shown in FIGS. 1 to 3.

Immediately before surgery proper, the patient under anesthetic is fitted with a urethro-bladder tube and placed in the gynecological position.

The surgeon incises the patient's perineal region vertically from, at the rear, the anus 114, and at the front, the scrotum 106, as indicated by reference $I_1$ in FIGS. 4 to 6. The front end of the incision $I_1$ is determined by using a finger to identify the bottom edge of the pubis 108, while the middle of the incision is identified by the bend formed by the urethra 116 where it extends towards the balder 112, this bend being shown up by the urethro-bladder tube. The incision $I_1$ passes upwards through the skin 122, and the subcutaneous fat 124 in the perineal region, and continues until it reaches the end bulb 118A of the spongy body 118, which is itself preserved. On either lateral side of this bulb, there can then be seen the whitish rounded portions in relief of the coat of the cavernous body 120. By palpation on either side of the bulb 118A, the surgeon then reveals the V-shaped groove between each cavernous body 120 and the spongy body 118.

At the bottom of each groove thus revealed in this way, the perineal membrane is incised in substantially sagittal manner, e.g. using an electric knife to a depth of about 1 cm, if possible without penetrating into the corresponding cavernous body 120, as represented by references $I_2$ in FIGS. 5 and 6. Using a finger, the surgeon gently releases the incised tissue of the membrane going round over the top of each cavernous body 120 so as to make contact with the corresponding ischiopubic branch 126 of the ilium 110 (FIG. 6).

Thereafter, the surgeon takes hold of the needle 10 and inserts it into the patient's body from the root of a first thigh 102. The point of entry of the pointed end 11 of the needle in the root of the thigh is advantageously situated simultaneously about 4 cm from the incision $I_1$ and about 4 cm from the bottom edge of the portion in relief of the abductor magnus muscle of the thigh. Because of its curved main portion 12, the needle 10 advances through the tissue of the patient while remaining on the same lateral side of the patient as his first thigh 102, until it reaches the corresponding obturator foramen 128 of the ilium, through which the pointed end 11 advances until it reaches the corresponding incision $I_2$. For this purpose, the surgeon inserts a finger in the incision $I_2$ so as to feel the pointed end 11 as it approaches and thus guide its exit through this incision.

Once the pointed end 11 of the needle has gone through the incision $I_2$, the implant 2 is secured to the needle via the fastener element 41 that engages in the groove 14, and then the needle is extracted by pulling its base portion 13 so that the end 11 moves in reverse along the path that brought it to the perineal region. The strips 20 and 30 are thus put into place in the body of the patient between a first one of the two incisions $I_2$ and the root of the first thigh 102 of the patient, passing through a first one of the two obturator foramens 128 of the ilium 110. The needle 10 is thus pulled outwards until the strip ends 20A and 30A project outside the patient from the root of his thigh. The surgeon then separates the strips from the needle, in particular by disconnecting the element 41.

Using the same needle 10 or an analogous needle, the surgeon performs symmetrical movements for the other lateral side of the patient. The needle is inserted from the root of the other thigh 102 until its pointed end 11 reaches and projects through the second incision $I_2$ in the membrane between the second cavernous body 120 and the spongy body 118, passing through the second obturator foramen 128. Thereafter, the strip ends 20E and 30E are secured to the pointed end 11 by means of the element 42. The needle is then pulled back out, moving the strips 20 and 30 into place in the patient's body between the second incision $I_2$ and the root of said other thigh 102, passing via the second obturator foramen 128, and with the strip ends 20E and 30E extending outside the patient from the root of its thigh. The strips 20 and 30 are then generally in the implantation configuration as shown in FIGS. 5 and 6, i.e. they have their middle portions 20C and 30C extending lengthwise generally perpendicularly to the mean sagittal plane of the urethra 116.

The surgeon then puts each of the strips 20 and 30 under tension, i.e., and as represented by arrows $F_{20}$, $F_{30}$ in FIG. 6, the surgeon pulls on the intermediate portions 20B & 20D, 30B & 30D of each strip, in practice acting on the terminations of the portions where they extend outside the roots of the patient's thighs, such that the strip middle portions 20C, 30C bear firmly against the spongy body 118 from the underside of said body. Each portion 20C, 30C is then U-shaped, with the spongy body 116 being supported in the bottom of the U-shape. The tension exerted on the implant 2 is adjusted so as to obtain obstructive support of the urethra 116, so as to treat incontinence. For this purpose, the surgeon advantageously tensions the strips 20 and 30 to differing extents, in particular in order to take account of the morphology and the pathology of the patient. Thus, by way of example, for a patient who has been subjected to a prostatectomy, the strip that is implanted closer to the bladder 112, i.e. the strip 20 in the example shown in FIGS. 5 and 6, is put into place with tension at greater intensity than the strip 30, for the purpose of firmly supporting or even slightly compressing the bulb 118A. Conversely, in certain clinical circumstances, it can be preferred to put the front strip under greater tension, in particular in order to limit any risk of the implant 2 subsequently migrating rearwards.

Whatever the way tension is adjusted in the strips 20 and 30, it will be understood that the middle strip portions 20C and 30C are alone in forming the support zone for the urethra 116, which explains why a value of about 3 cm is appropriate for the length $L_C$. In this respect, the fact that the stitched connection between the portions 20C and 30C takes place solely at the longitudinal ends of said portions, via the lines of stitching 51, 52 ensures that no stitches are pressed too firmly against the tissue below the urethra, and encourages uniform behavior of each of the strips 20, 30 over the entire length of its middle portion 20C, 30C. In addition, by means of the implant 2, action is taken on the urethra 116 over an implant width that is double compared with the individual width of either strip 20 and 30, thereby taking advantage of the moderate individual widths of the strips for their passage through the obturator foramen, as described above, thus limiting as much as possible the transverse extent of the tissue through which these strips pass.

Once the surgeon has adjusted the tension of the implant 2, the implant can, where necessary, be anchored in the patient's tissue to avoid relaxing its effect on the urethra 116. This anchoring is not always necessary, depending on the morphology and the pathology of the patient being treated since the fringes 25, 26, 35, and 36 in the intermediate strip portions 20B, 30B, 20D, and 30D tend to prevent the strips from moving in the tissues through which the strips pass, by clinging onto said tissues. When additional anchoring is desired, the surgeon uses a suture to secure one and/or the other of the knits 21 and 31 to tissues of the patient. Preferably, it is the middle portions 20C and 30C that are thus secured to the spongy body 118, at spot connection zones between the chains 23 and/or 33 and the body 118. Advantageously, these connection zones are four in number forming a rectangular pattern with the anteroposterior midline thereof lying substantially in the sagittal midplane of the urethra 116. Other numbers and other patterns could be envisaged for these connection zones.

The surgery is then terminated: the terminal portions of the strips 20 and 30 that were brought out through the roots of the thighs 102 are cut off and the perineal incision $I_1$ is closed in layers, possibly after prior closure of each incision $I_2$, where necessary.

In a variant of the above-described surgical method, the step of applying traction to the strips 20 and 30 in order to adjust their tension, and the optional step of securing these strips by suturing can be performed in the opposite order, or they can be performed simultaneously.

Various improvements and variants can doubtless be envisaged to the kit 1 and to the method of treatment described above. As examples:

for the implant 2 shown in the figures, the strips 20 and 30 present the same width that is substantially constant over the entire length of each strip, which constitutes an embodiment that is practical to fabricate and to handle during implantation; nevertheless, in a variant that is not shown, one of the two strips could be wider than the other, and it is not impossible for the width of one and/or the other of the strips to vary along its length; thus, the chains 23 and/or 33 in the knits 21 and 31 could be present in a number that is greater than or less than four;

for the implant 2 described above, the mechanical connection between the strips 20 and 30 relies on lines of stitches 51, 52, and 53, which advantageously and effectively take advantage of the knitted structure of the strips; nevertheless, particularly if the non-extensible property of the strips 20 and 30 relies on a structure other than a knit, it is not impossible for the mechanical connections between the middle portions of the strips at each of the ends of the strips to be made by other means, e.g. by means of an adhesive material, a swaged sheath, etc.;

various embodiments can be envisaged concerning the connection means 40; the reader may refer to document EP-A-1 342 450 in the name of the Applicant to discover details and variant embodiments of such means, and also corresponding arrangements for the needle 10; and/or needles of the type 10 described above are preferably used for implanting the implant 2 in the body of a patient, but it should be understood that other instruments suitable for putting the strips 20 and 30 into place could also be used.

What is claimed is:

1. An implant for supporting a urethra of a man for treating urinary incontinence, which implant comprises, two separate elongate flexible first and second strips that are substantially inextensible in a length direction between two opposite ends of each of the first and second strips and that include respective middle portions that are disposed parallel to one another and have respective side edges that are adjacent and face towards one another, the first and second strips being connected to each other at their middle portion so that a width of the implant at the respective middle portions is equal to a combined width of the middle portions of the first and second strips, wherein each of the first and second strips also includes intermediate portions that extend between the middle portion and each of the opposite ends of each strip, wherein the first and second strips are separate from each other along the intermediate portions thereof, the middle portion and the intermediate portions of the first strip have a uniform width and the middle portion and the intermediate portions of the second strip have a uniform width, and a mechanical connection extending transversely relative to the length direction of the first and second strips which connects the middle portions of the first and second strips at at least opposite longitudinal ends of the middle portions of the first and second strips.

2. An implant according to claim 1, wherein the first and second strips are also mechanically connected to each other at their respective two opposite ends, each pair of the connected ends being provided with a joint fastener element for connecting the first and second strips together to an instrument for implanting the implant.

3. An implant according to claim 2, wherein each of the first and second strips is constituted by a yarn knit including longitudinal reinforcing chains and an intermediate trellis connecting the chains together transversely, and wherein at each pair of the connected ends of the first and second strips, the knits of the first and second strips are sewn to the joint fastener element.

4. A surgical kit for treating urinary incontinence in a man, which kit comprises:

an implant as set forth in claim 2 for supporting the urethra of a patient; and at least one instrument for implanting the implant and that is adapted to co-operate with at least one of the two joint fastener elements.

5. The surgical kit for treating urinary incontinence in a man of claim 4 wherein the instrument for implanting the implant is an implantation needle.

6. The implant according to claim 2 wherein the instrument for implanting the implant is an implantation needle.

7. An implant according to claim 1, wherein each of the first and second strips is constituted by a yarn knit including longitudinal reinforcing chains and an intermediate trellis connecting the chains together transversely.

8. An implant according to claim 7, wherein the mechanical connection includes stitching connecting at least one of the chains of the middle portion of one of the first and second strips to at least one of the chains of the middle portion of the other of the first and second strips.

9. An implant according to claim 8, wherein the the stitching includes two lines of stitches that extend transversely relative to the chains at the opposite longitudinal ends of the middle portions.

10. An implant according to claim 7, wherein each of the first and second strips is bordered by two lateral fringes for clinging to tissues in which the implant is implanted, and wherein the two fringes that face each other in the middle portions of the two strips are intermingled.

11. An implant according to claim 1, wherein the middle portions of the first and second strips have a longitudinal size that is less than 8 cm.

12. An implant according to claim 1, wherein the uniform width of the middle and the intermediate portions of each of the first and second strips are the same.

13. The implant of claim 1 wherein the middle portions of the first and second strips have a longitudinal size in a range of 2 cm to 4 cm.

14. The implant of claim 1 wherein the mechanical connection includes an adhesive material.

15. The implant of claim 1 wherein the mechanical connection includes a swaged sheath.

16. A surgical method for treating urinary incontinence in a man, by means of an implant for supporting the urethra of a patient, the implant comprising first and second distinct elongate flexible strips that are substantially inextensible in a length direction between two opposite ends of each of the first and second strips and that include respective middle portions that are disposed parallel to one another and have respective side edges that are adjacent and face towards one another, the first and second strips being connected to each other at their middle portion so that a width of the implant at the middle portions is equal to a combined width of the respective middle portions of the first and second strips, wherein each of the first and second strips also includes intermediate portions that extend between the middle portion and each of the opposite ends of each of the first and second strips, wherein the first and second strips are separate from each other along the intermediate portions thereof, the middle portion and the intermediate portions of the first strip have a uniform width and the middle portion and the intermediate portions of the second strip have a uniform width, and a mechanical connection extending transversely relative to the length direction of the first and second strips which connects the middle portions of the first and second strips at at least opposite longitudinal ends of the middle portions of the first and second strips;

said method comprising the steps of:

i) vertically incising skin and subcutaneous fat in a perineal region of a patient between his scrotum and his anus, as far as the bulb of his urethral spongy body, while preserving the spongy body;

ii) in the perineal incision made during step i), separating on either lateral side of the urethral spongy body, two cavernous bodies of the patient;

iii) sagittally incising perineal membrane between each of the two cavernous bodies and the urethral spongy body;

iv) putting the implant into place in the patient's body in such a manner that the middle portions of the first and second strips extend under and across the urethral spongy body, while from each side of these middle portions in the length direction, the corresponding respective intermediate portions of the first and second strips extend from the incision in the perineal membrane made during step iii) to a root of a corresponding thigh of the patient, passing via a corresponding obturator foramen of the patient's ilium, the ends of the first and second strips extending outside the patient from the roots of the thighs;

v) pulling on the intermediate portions of the first and second strips in such a manner as to cause the middle portions to act on the urethral spongy body over the combined width of the middle portions of the first and second strips so as to bear under tension against the urethral spongy body, the intensities of the traction applied respectively to the first and second strips being adjustable independently of each other; and vi) cutting off the portions of the first and second strips that extend out from the roots of the thighs, and thereafter closing the perineal incision made in step i).

\* \* \* \* \*